(12) United States Patent
Hoy et al.

(10) Patent No.: US 6,506,409 B1
(45) Date of Patent: Jan. 14, 2003

(54) DOSAGE DEVICE

(75) Inventors: John Hoy, Rivonia (ZA); Phillipus Jansen Van Rensburg, Randburg (ZA)

(73) Assignee: Plaaskem (Pty) Limited, Sandton (ZA)

( * ) Notice: Subject to any disclaimer, the term of this patent is extended or adjusted under 35 U.S.C. 154(b) by 0 days.

(21) Appl. No.: 09/485,927

(22) PCT Filed: Aug. 21, 1998

(86) PCT No.: PCT/GB98/02521

§ 371 (c)(1),
(2), (4) Date: Feb. 18, 2000

(87) PCT Pub. No.: WO99/09823

PCT Pub. Date: Mar. 4, 1999

(30) Foreign Application Priority Data

Aug. 22, 1997 (ZA) .............................. 97/7579

(51) Int. Cl.$^7$ .......................... A61K 9/14; A61K 47/00
(52) U.S. Cl. ...................... 424/489; 424/400; 424/439; 424/464; 424/468; 514/937; 514/951; 514/952; 514/960
(58) Field of Search ................................ 424/464, 468, 424/469, 489; 514/937, 951, 952, 960

(56) References Cited

U.S. PATENT DOCUMENTS 3,330,729 A * 7/1967 Johnson, Jr. ................. 424/468
4,172,714 A * 10/1979 Albert ............................ 71/93

FOREIGN PATENT DOCUMENTS

| DE | 25 12 247 A1 | 10/1976 | |
|---|---|---|---|
| DE | 41 09 921 C1 | 11/1992 | |
| EP | 0 777 964 A1 | 6/1997 | |
| WO | WO 93/13658 | * 7/1993 | ................. 424/468 |

OTHER PUBLICATIONS

Riverside Webster's II, New College Dictionary, 1995 by Houghton Mifflin Company, p. 328.*

* cited by examiner

Primary Examiner—Thurman K. Page
Assistant Examiner—Charesse Evans
(74) Attorney, Agent, or Firm—Jeffrey S. Melcher; Manelli Denison & Selter, PLLC

(57) ABSTRACT

A method of making a dosage device comprises mixing a suspension concentrate comprising at least one active ingredient which is in solid form at 25° C., and which has an average particle size of less than 10 microns, in a carrier liquid in which the active ingredient is non-soluble or sparingly soluble, and a drying agent for the carrier liquid. The drying agent takes up at least some of the carrier liquid of the suspension concentrate, thereby to dry the active ingredient at least partly and to obtain a mixture comprising the active ingredient and the drying agent. The mixture is compressed into at least one unitary dosage device.

23 Claims, No Drawings

DOSAGE DEVICE

THIS INVENTION relates to a dosage device. It relates also to a method of forming a dosage device, and to a method of treating an article or locus.

EP 0 777 964 A discloses a method of making a dosage device which comprises admixing at least one active ingredient which is a pesticide which is in solid form at 25° C., is sparingly soluble in water, and which has an average particle size of less than 5 microns, with a disintegrating agent, to provide a compressible mix; and compressing the compressible mix into a unitary dosage device capable of disintegrating in water to form a suspension of said active ingredient in the water. Neither suspension preparation techniques nor drying agents are used.

DE 25 12 247 A describes making stabilized tablets containing moisture-sensitive ingredients but in which the particle size is relatively large.

U.S. Pat. No. 4,172,714 A discloses the preparation of a herbicide composition in which the particle size is also relatively large, the herbicide being applied in the form of relatively large pellets so that the herbicide is applied in concentrated form at relatively few loci.

WO 93 13658 A describes pesticide tablets with an internal dessicant.

DE 41 09 921 C1 discloses the preparation of a solid product but without a compaction step and particle sizes of the components are relatively large.

According to a first aspect of the invention, there is provided a method of making a dosage device, which method comprises mixing a suspension concentrate comprising at least one active ingredient which is in solid form at 25° C., and which has an average particle size of less than 10 microns, in a carrier liquid in which the active ingredient is non-soluble or sparingly soluble, and a drying agent for the carrier liquid, such that the drying agent takes up at least some of the carrier liquid of the suspension concentrate, thereby to dry the active ingredient at least partly and to obtain a mixture comprising the active ingredient and the drying agent; and compressing the mixture into at least one unitary dosage device.

The method may include forming the suspension concentrate by mixing the active ingredient and the carrier liquid. The method may include communiting the active ingredient in solid form and having an average particle size greater than 10 microns, to have an average particle size of less than 10 microns. The active ingredient may be comminuted sufficiently to have an average particle size less than 5 microns, and even less than 3 microns, e.g. less than 1 micron. The comminution may be effected by wet milling the suspension concentrate, eg in a bead mill, to obtain the desired active ingredient particle size.

While, at least in principle, any carrier liquid in which the active ingredient is insoluble or sparingly soluble, can be used, the carrier liquid is preferably water.

The drying agent or dessicant may be an at least partially anhydrous substance. The at least partially anhydrous substance may be an anhydrous salt which takes up the carrier water as water of hydration. The anhydrous salt may be selected from the group comprising anhydrous magnesium sulphate, anhydrous sodium sulphate, anhydrous sodium acetate, and anhydrous calcium chloride. A molar excess of the anhydrous salt over the carrier water present in the suspension concentrate, may be used. For example, the molar proportion of anhydrous salt to carrier water may be about 2:1 to 2.5:1. However, it is envisaged that in some instances the proportion of anhydrous salt used need not necessarily be a molar excess over the carrier water present. For example, certain anhydrous salts can take up more than an equimolar quantity of water of hydration.

The method may include adding to the suspension concentrate and/or to the mixture a further substance capable of reaction with some of the water present in the suspension concentrate, thereby also to dry the active ingredient The further substance may be an oxide which is capable of reacting with water to form a hydroxide. The further substance may be magnesium oxide and/or calcium oxide. The magnesium oxide and/or calcium oxide may thus replace some of the anhydrous substance which is used. For example, when used, it may typically replace in the order of 25% to 50% by mass of the anhydrous substance which is used.

The method may include adding a dispersing agent for the active ingredient and/or an anti-foaming agent and/or an anti-settling agent to the suspension concentrate before and/or after comminution thereof.

Thus, the suspension concentrate may comprise the active ingredient, the dispersing agent, the anti-foaming agent, the anti-settling agent, and water as carrier for the other components. More preferably, the suspension concentrate may comprise

| Component | % (m/m) |
|---|---|
| active ingredient | about 40 to 50 |
| dispersing agent | about 7 |
| anti-foaming agent | <1 |
| anti-settling agent | <1 |
| water | balance |

The dispersing agent may be a surfactant such as that conventionally used in a wettable powder or suspension concentrate formulation, for example a lignosulphonate such as sodium lignosulphonate or that available from Borregaard under the trade name Borresperse CA; sodium naphthalene sulphonic acid/formaldehyde condensate; sodium alkyl aryl sulphonate; a nonyl phenol alkylene oxide, such as nonyl phenol ethylene oxide condensate or nonyl phenol ethylene/propylene oxide such as SYNPERONIC NPE 1800 (trade name), available from ICI; alcohol ethylene/propylene oxide condensate; a sodium lauryl sulphate which also acts as wetting agent, such as that available under the trade name EMPICOL LZ from Lankro; a sodium diisopropyl naphthalene sulfonate which also acts as wetting agent, such as that available under the trade name AEROSOL OS from Cyanamid; a sodium salt of naphthalene sulfonic acid formaldehyde condensate, such as that available under the trade name TAMOL NNO or TAMOL DN from BASF; oxyethylated polyarylphenol phosphate, which is a dispersing agent in aqueous media, and an example of which is obtainable under the trade name SOPROPHOR FL from Rhone-Poulenc; or the like.

While the active ingredient can be any suitable active ingredient, such as a therapeutic agent, anthelmintic, a pigment or dye, or the like, the Applicant believes that the method will find particular, but thus not necessarily exclusive, application in making dosage devices in which the active ingredient is a pesticide, eg an insecticide, herbicide, fungicide, acaricide, or the like.

The active ingredient may thus be a pesticide which is sparingly soluble in water, with water hence being the carrier liquid for use in forming the suspension concentrate, as hereinbefore described. The pesticide may have a water solubility of less than 1000 mg/l at 25° C., preferably less than 50 mg/l at 25° C. Preferably, the pesticide should have a melting point exceeding 70° C.

The pesticide may be a herbicide such as atrazine, simazine, cyanazine, terbuthylazine, diuron, chlorsulphuron, metsulfuron, tralkoxydin, or 2-(2-chloro-4-mesylbenzoyl)cyclohexane-1,3-dione; an insecticide such as deltamethrin, lindane, carbaryl, endosulfan, or carbofuran; a fungicide such as thiophanate methyl, carbendazim, flutriafol, hexaconazole, chlorothalonil, copper oxychloride, captan or thiram; or an acaricide such as hexythiazox, cyhexatin, amitraz or acrinathrin.

The method may include adding a disintegrating agent to the mixture before compressing it into the unitary dosage device.

The disintegrating agent may be capable of disintegrating by effervescing or swelling on contact with water. When it is capable of swelling on contact with water, it may be a cross-linked polyvinyl pyrrolidone which also acts as a binder. For example, the cross-linked polyvinylpyrrolidone may then be that available under the trade name POLYPLASDONE XL from GAF Corp., or that available under the trade name KOLLIDON CL from BASF. However, it can instead be any other suitable disintegrating agent capable of swelling on contact with water such as a modified cellulose gum, for example that available under the trade name AC-DI-SOL from FMC Corporation; a sodium starch glycolate such as that available under the trade name EXPLOTAB from Protea Chemical Services; or a microcrystalline cellulose binder such as that available under the trade name Avicel PH101 from FMC Corp. When it is capable of effervescing on contact with water, it may be an acid and base combination such as tartaric acid and an alkali metal carbonate or bicarbonate, eg sodium bicarbonate.

The method may also include adding one or more of the following to the mixture or to the suspension concentrate before admixture of the anhydrous salt therewith:

a further surfactant, such as that hereinbefore described, to inhibit recompaction of the active ingredient;

an absorptive carrier such as a colloidal silica, for example AEROSOL 200 (trade name), diatomaceous earth, or a clay such as attapulgite;

a binder such as a microfine cellulose, for example that obtainable under the trade name ELCEMA P100 from Degussa, and which also acts as a filler and disintegrating agent; or lactose monohydrate for example that obtainable under the trade name LUDIPRESS from BASF, and which is also a direct tabletting auxiliary;

a lubricant such as magnesium stearate;

a flow improving agent such as an absorptive silica, for example SIPERNAT 22S (trade name) from Degussa, which is a spray-dried ground silica, and acts as a free flow-anti-caking agent; and a water soluble filler such as soluble starch, urea, or sodium chloride.

The mixture may thus comprise the suspension concentrate, the further surfactant, the anhydrous salt, and the disintegrating agent. More particularly, the mixture may comprise

| Component | % (m/m) |
|---|---|
| suspension concentrate | 25 to 40 |
| filler/surfactant/dispersant | about 8 |
| anhydrous salt | 30 to 40 |
| binder/disintegrating agent | 12 to 37 |

The mixture is, if necessary, rendered into compressible form. The mixture may be allowed to stand for a sufficient period of time until the hydration of the salt, ie the water absorption, has been completed, thereby also to render it compressible. The water absorption or hydration period will depend on the anhydrous salt used, but can typically vary from about 12 hours to about 72 hours. If necessary, the mixture can be comminuted, eg milled, prior to compressing it. The method is, however, characterized thereby that drying of the mixture at elevated temperature prior to compressing it, is not required.

The invention also extends to a dosage device when made in accordance with the method of the first aspect of the invention.

According to a second aspect of the invention, there is provided a dosage device which is in compressed unitary form and which comprises an admixture of an active ingredient which is in solid form at 25° C. and which has an average particle size of less than 10 microns, and a substance which is capable of being in anhydrous form, and which is at least partially hydrated in the dosage device. The dosage device may be as hereinbefore described.

According to a third aspect of the invention, there is provided a method of treating an article or locus, which comprises introducing a dosage device according to any one of claims 13 to 19 inclusive, into a predetermined volume of water, with the volume of water being such that the concentration of the active ingredient in the water is greater than the solubility limit of the active ingredient in the water;

allowing the dosage device to disintegrate, thereby to form a suspension of the active ingredient in the water; and applying the suspension to an article or locus to be is treated.

The invention will now be described by way of the following non-limiting examples.

EXAMPLE 1

A) Preparation of Suspension Concentrate

A suspension concentrate containing 50% (m/m) deltamethrin was made up by admixing, in a Dyno (trademark) mill the following components in the mass proportions indicated. The Dyno mill is a bead mill comprising a static casing within which rotates a rotor such that the rotor has a peripheral speed of 10–15 m/sec. The mill is filled up to a level of about 85% by volume with 1mm glass beads.

| Component | % (m/m) |
|---|---|
| Deltamethrin tech 98, 5%, as active ingredient | 50.76 |
| Synperonic NPE 1800 (trademark), available from ICI, as dispersing agent | 6.60 |
| Silcolapse 5000 A (trademark), an anti-foaming agent available from Rhone-Poulenc | 0.10 |

B) Preparation of Tablets in Accordance with the Invention

A tablet was formulated, using the procedure set out hereunder, to have the following composition:

| Component | % (m/m) |
| --- | --- |
| Kelzan D (trademark), an anti-settling agent, available from Kelco Inc | 0.04 |
| Water | 42.50 |

| Component | % (m/m) |
| --- | --- |
| Deltamethrin 50% (m/m) suspension concentrate, obtained in (A) | 40.00 |
| Tamol DN (trademark), a surfactant available from BASF | 8.00 |
| Anhydrous magnesium sulphate | 40.00 |
| Kollidon CL (trademark), a disintegrant available from BASF | 12.00 |

The Tamol DN was dissolved in the suspension concentrate under stirring in a planetary mixer. Thereafter the anhydrous magnesium sulphate was added as a single addition. The mixture was stirred until it had dried into crumbly granules. The mixer was switched off, covered and left overnight for the hydration reaction of magnesium sulphate to proceed to completion, ie for water absorption to be effected. The water absorption period was thus about 12 hours. Thereafter, the mixture was stirred briefly to loosen the caked dry granules into pieces small enough to be introduced into a mill. The bone dry granules were milled in a hammer-type mill having a 1–2 mm screen. The Kollidon CL was added to the powdered concentrate, and mixed therewith in the mill. The resultant homogeneous mixture was introduced into a tabletting machine, and pressed into 2 g tablets at about 5 MPa pressure.

The resultant tablets thus had the following composition:

| Component | % (m/m) |
| --- | --- |
| Deltamethrin active | 20.00 |
| Impurities | 0.30 |
| Synperonic NPE 1800 | 2.64 |
| Silcolapse 5000 A | 0.04 |
| Kelzan D | 0.02 |
| Magnesium sulphate anhydrous | 40.00 |
| Tamol DN | 8.00 |
| Kollidon CL | 12.00 |
| Water | 17.00 |

Anhydrous magnesium sulphate can take up water, to form water of hydration thereof, in a molar ratio of up to 7 mols of water for 1 mol of magnesium sulphate. Thus the anhydrous magnesium sulphate used is in a theoretical excess, on a mass basis, of about 2:1. This is to ensure that all water present in the suspension concentrate is taken up by the anhydrous magnesium sulphate. The use of the anhydrous magnesium sulphate thus dries the suspension concentrate sufficiently for compressing thereof into tablets to be feasible without further drying thereof at elevated temperature being required.

The tablets, when introduced into water at the rate of one tablet in 5 liters of water, disintegrate within 1 minute. Microscopic examination revealed that most of the particles in the suspension were in the 0.5–2 micron range.

Examples 2, 3 and 4 hereunder were prepared in identical fashion to Example 1, apart therefrom that the constituents differed from those of Example 1, as given in the examples. Additionally, in Examples 2 and 3 the water absorption period was 72 hours.

EXAMPLE 2

| Component | % (m/m) |
| --- | --- |
| Deltamethrin 50% (m/m) suspension concentrate | 40.00 |
| Tamol DN | 8.00 |
| Anhydrous sodium sulphate | 40.00 |
| Kollidon C L | 12.00 |

A 2.5 g tablet was pressed at about 5 MPa pressure. This tablet was much harder than the tablet of Example 1, ie the tablet containing magnesium sulphate. When introduced into water at the rate of one tablet in 5 liters of water, the disintegration time was about 4½ minutes. Microscopic examination revealed that most of the particles in the suspension were in the 0.5–2 micron range.

EXAMPLE 3

| Component | % (m/m) |
| --- | --- |
| Deltamethrin 50% (m/m) suspension concentrate | 40.00 |
| Tamol DN | 8.00 |
| Anhydrous sodium acetate | 40.00 |
| Kollidon C L | 12.00 |

A 2.5 g tablet was pressed at about 5 MPa pressure. The tablet was softer than the tablet of Example 2, ie the tablet containing sodium sulphate. When introduced into water at the rate of one tablet in 5 liters of water, the disintegration time was about 2 minutes. Microscopic examination revealed that most of the particles in the suspension were in the 0.5–2 micron range.

EXAMPLE 4

A 2.0 g tablet was also prepared using a proprietary acaricide product.

| Component | % (m/m) |
| --- | --- |
| Acrinathrin 40% (m/m) suspension concentrate obtainable from Hoechst Schering AgrEvo SA and containing 50% (m/m) water | 25.0 |
| Borresperse C A, a lignosulphate dispersant obtainable from Borregaard | 8.0 |
| Anhydrous magnesium sulphate | 30.0 |
| Kollidon C L | 5.0 |
| Avicel PH 101, a microcrystalline cellulose binder obtainable from FMC Corp | 32.0 |

The resulting tablet has satisfactory properties when diluted or dispersed in water.

The Applicant has found that with active pesticides requiring a very low rate of application, typically in the order of a few grams per hectare, very small pesticide particles, typically having an average particle size less than 5 microns, and even less than 1 micron, dispersed in the prescribed carrier liquid, usually water, are highly desirable for effective, accurate and even distribution of the pesticide on application. Furthermore, the smaller the particle size, the greater the surface area thereof, which promotes effective release of the pesticide after application to a locus or substrate. However, it has hitherto been a problem when providing pesticides in tablet form, that if the pesticide particles are too small, unsatisfactory dispersion rates of the tablet in the carrier liquor result. However, it has surprisingly been found that in the method and dosage device of the present invention in which the average pesticide particle size is less than 5 microns, and typically in the order of 1 to 3 microns, or even less than 1 micron, rapid disintegration and dispersion rates are achieved. Moreover, the resulting tablets have adequate hardness which permit handling in the field, and the tablets on dispersion have excellent suspension properties.

The dosage devices of the present invention thus provide a good vehicle for such pesticides, since they are compact and hence easily transported and stored, and are also in a form in which they are handled safely. Furthermore, there is not a problem of having to dispose of large used pesticide containers. They are furthermore easy to disperse and apply effectively and accurately as set out hereinbefore, ie with little wastage.

Furthermore, the Applicant was also surprised to find that the resulting average pesticide particle size of the active ingredient, after the tablets had been dispersed in water, was of the desired order less than 3 microns in spite of the fact that the active ingredient, after having been milled down to less than 5 microns, was then compressed with the disintegrating agent into tablet form during which agglomeration into larger particle sizes would have been expected. However, as stated, it was surprisingly found that the average particle size of the active ingredient, in the resultant suspensions, was still in the range of 0.5–3 microns.

The Applicant believes that the method of the invention, which does not require drying of the formulation in a drying oven before forming into tablets, has advantages over tablets formulated using such a drying step, particularly as regards capital and operating costs. Thus, the need to provide an oven is avoided. Operating costs associated with such an oven, such as heating costs and labour costs for loading and unloading the oven, are also avoided.

What is claimed is:

1. A method of making a dosage device, which method comprises mixing a suspension concentrate comprising at least one active ingredient which is in solid form at 25° C., and which has an average particle size of less than 10 microns, in a carrier liquid in which the active ingredient is non-soluble or sparingly soluble, and a drying agent for the carrier liquid, such that the drying agent takes up at least some of the carrier liquid of the suspension concentrate, thereby to dry the active-ingredient at least partly and to obtain a mixture comprising the active ingredient and the drying agent; and compressing the mixture into at least one unitary dosage device.

2. A method according to claim 1, which includes forming the suspension concentrate by mixing the active ingredient in solid particulate form and having an average particle size greater than 10 microns, and the carrier liquid, and wet milling the suspension concentrate to comminute the active ingredient so that it has an average particle size of less than 10 microns.

3. A method according to claim 2, wherein the carrier liquid is water, and wherein the drying agent is an at least partially anhydrous substance.

4. A method according to claim 3, wherein the at least partially anhydrous substance is an anhydrous salt which takes up the carrier water as water of hydration, and which is selected from the group consisting of anhydrous magnesium sulphate, anhydrous sodium sulphate, anhydrous sodium acetate, and anhydrous calcium chloride.

5. A method according to claim 3, which includes adding at least one of to the suspension concentrate or to the mixture a further substance capable of reaction with some of the water present in the suspension concentrate, thereby also to dry the active ingredient.

6. A method according to claim 5, wherein the further substance is an oxide which is capable of reacting with water to form a hydroxide.

7. A method according to claim 6, wherein the further substance is at least one of magnesium oxide or calcium oxide.

8. A method according to claim 3, which includes adding a dispersing agent for at least one of the active ingredient or an anti-foaming agent or an anti-settling agent to the suspension concentrate at least one of before or after comminution thereof.

9. A method according to claim 3, wherein the active ingredient is a pesticide having a water solubility of less than 1000 mg/l at 25° C., and a melting point which exceeds 70° C.

10. A method according to claim 3, which includes, if necessary, rendering the mixture into compressible form, and which includes adding a disintegrating agent to the mixture before compressing it into the unitary dosage device.

11. A method according to claim 10, wherein the mixture comprises

| Component | % (m/m) |
|---|---|
| suspension concentrate | 25 to 40 |
| filler/surfactant/dispersant | about 8 |
| anhydrous substance | 30 to 40 |
| disintegrating agent | 12 to 37 |

12. A method according to claim 10, which includes allowing the mixture to stand for a sufficient period of time until the hydration of the salt has been completed, thereby also to render it compressible, and, if necessary, comminuting the mixture prior to compressing it.

13. A dosage device when made in accordance with the method as claimed in claim 1 inclusive.

14. A dosage device which is in compressed unitary form and which comprises an admixture of an active ingredient which is in solid form at 25° C. and which has an average particle size of less than 3 microns, and a substance which is capable of being in anhydrous form, and which is at least partially hydrated in the dosage device.

15. A dosage device according to claim 14, wherein the substance is an anhydrous salt and is selected from the group consisting of anhydrous magnesium sulphate, anhydrous sodium sulphate, anhydrous sodium acetate, and anhydrous calcium chloride.

16. A dosage device according to claim 14 or claim 15, which includes an oxide which is capable of reacting with water to form a hydroxide.

17. A dosage device according to claim 16, wherein the oxide at least one of is magnesium oxide and/or calcium oxide.

18. A dosage device according to claim 14, which includes a dispersing agent for the active ingredient or an anti-foaming agent or an anti-settling agent or a disintegrating agent.

19. A dosage device according to claim 14, wherein the active ingredient is a pesticide having a water solubility of less than 1000 mg/l at 25° C., and a melting point which exceeds 70° C.

20. A method of treating an article or locus, which comprises
   introducing a dosage device according to claim 14, into a predetermined volume of water, with the volume of water being such that the concentration of the active ingredient in the water is greater than the solubility limit of the active ingredient in the water;
   allowing the dosage device to disintegrate, thereby to form a suspension of the active ingredient in the water; and
   applying the suspension to an article or locus to be treated.

21. A pesticide tablet or pellet which disperses in a water carrier to form a suspension of the pesticide, the pesticide tablet or pellet comprising:
   at least one pesticide which is in solid form at 25° C., having an average particle size of less than 10 microns, and having a water solubility of less than 1000 mg/L at 25° C.; and
   at least one drying agent which is capable of being in anhydrous form and which is at least partially hydrated, wherein the pesticide tablet or pellet has been formed by forming a suspension of the pesticide in water, adding the drying agent to the suspension such that the drying agent becomes at least partially hydrated by taking up at least a portion of the water, and compressing the resulting mixture to form the pesticide tablet or pellet.

22. A method of treating an article or locus with a pesticide, the method comprising:
   disintegrating a pesticide tablet or pellet in water to form a suspension of the pesticide in water, the volume of water being such that the concentration of the pesticide in the water is greater than the solubility limit of the pesticide in the water; and
   applying the suspension to an article or locus, wherein the pesticide tablet or pellet comprising at least one pesticide which is in solid form at 25° C., having an average particle size of less than 10 microns, and having a water solubility of less than 1000 mg/L at 25° C., and at least one drying agent which is capable of being in anhydrous form and which is at least partially hydrated, wherein the pesticide tablet or pellet has been formed by forming a suspension of the pesticide in water, adding the drying agent to the suspension such that the drying agent becomes at least partially hydrated by taking up at least a portion of the water, and compressing the resulting mixture to form the pesticide tablet or pellet.

23. A method of making a dosage device, which method comprises:
   mixing a suspension concentrate comprising at least one active ingredient, which is in solid form at 25°, having an average particle size of less than 3 microns, in a carrier liquid in which the active ingredient is non-soluble or sparingly soluble, with at least one drying agent for the carrier liquid, such that the drying agent takes up at least a portion of the carrier liquid of the suspension concentrate, thereby to dry the active ingredient at least partially and to obtain a mixture comprising the active ingredient and the drying agent; and
   compressing the mixture of active ingredient and drying agent into a dosage device.

* * * * *